United States Patent [19]

Becker et al.

[11] Patent Number: 5,500,434
[45] Date of Patent: Mar. 19, 1996

[54] COMBINATION OF ANGIOTENSIN-CONVERTING ENZYME INHIBITORS WITH CALCIUM ANTAGONISTS AS WELL AS THEIR USE IN DRUGS

[75] Inventors: Reinhard Becker, Wiesbaden; Henning: Rainer, Hattersheim am Main; Wolfgang Rüger, Kelkheim; Volker Teetz, Hofheim am Taunus; Hansjörg Urbach, Kronberg/Taunus, all of Germany

[73] Assignee: Hoechst Aktiengesellschaft, Frankfurt am Main, Germany

[21] Appl. No.: 225,762

[22] Filed: Apr. 11, 1994

Related U.S. Application Data

[60] Continuation of Ser. No. 811,149, Dec. 20, 1991, abandoned, which is a division of Ser. No. 358,427, May 30, 1989, Pat. No. 5,098,910, which is a continuation of Ser. No. 102,660, Sep. 30, 1987, abandoned.

[30] Foreign Application Priority Data

Oct. 2, 1986 [DE] Germany .......................... 36 33 496.0

[51] Int. Cl.$^6$ .................... A61K 31/44; A61K 31/40
[52] U.S. Cl. .................... 514/356; 514/419; 514/929
[58] Field of Search .................... 514/307, 356, 514/412, 419, 929

[56] References Cited

U.S. PATENT DOCUMENTS

| | | | |
|---|---|---|---|
| 4,374,847 | 2/1983 | Gruenfeld | 424/274 |
| 4,404,206 | 9/1983 | Vincent et al. | 514/307 |
| 4,508,729 | 4/1985 | Vincent et al. | 548/452 |
| 4,525,301 | 6/1985 | Henning et al. | 260/112.5 |
| 4,558,064 | 12/1985 | Teetz et al. | 514/409 |
| 4,558,065 | 12/1985 | Urbach et al. | 514/412 |
| 4,562,202 | 12/1985 | Urbach et al. | 514/423 |
| 4,584,294 | 4/1986 | Ruyle | 514/214 |
| 4,587,258 | 5/1986 | Gold et al. | 514/249 |
| 4,591,598 | 5/1986 | Urbach et al. | 514/412 |
| 4,614,805 | 9/1986 | Urbach et al. | 548/427 |
| 4,620,012 | 10/1986 | Henning et al. | 548/411 |
| 4,624,962 | 11/1986 | Henning et al. | 514/412 |
| 4,634,716 | 1/1987 | Parsons et al. | 514/338 |
| 4,659,838 | 4/1987 | Lerch | 548/452 |
| 4,668,796 | 5/1987 | Geiger et al. | 548/452 |
| 4,668,797 | 5/1987 | Urbach et al. | 548/452 |
| 4,672,071 | 6/1987 | Clark et al. | 514/356 |
| 4,684,662 | 8/1987 | Henning et al. | 548/452 |
| 4,691,022 | 9/1987 | Henning et al. | 548/408 |
| 4,703,038 | 10/1987 | Garthoff et al. | 514/19 |
| 4,705,797 | 11/1987 | Nardi et al. | 514/356 |
| 4,714,708 | 12/1987 | Urbach et al. | 514/412 |
| 4,727,160 | 2/1988 | Teetz et al. | 548/452 |
| 4,761,420 | 8/1988 | Gemain | 514/356 |
| 4,808,573 | 2/1989 | Gold et al. | 514/19 |
| 4,818,749 | 4/1989 | Gold et al. | 514/19 |
| 4,822,894 | 4/1989 | Geiger et al. | 548/257 |
| 4,831,157 | 5/1989 | Gold et al. | 548/452 |
| 5,098,910 | 3/1992 | Becker et al. | 514/299 |
| 5,256,687 | 10/1993 | Becker et al. | 514/419 |

FOREIGN PATENT DOCUMENTS

| | | |
|---|---|---|
| 0012401 | 7/1980 | European Pat. Off. . |
| 0018549 | 11/1980 | European Pat. Off. . |
| 0037231A2 | 10/1981 | European Pat. Off. . |
| 0012845 | 3/1982 | European Pat. Off. . |
| 0046953 | 3/1982 | European Pat. Off. . |
| 0049658 | 4/1982 | European Pat. Off. . |
| 0050800A1 | 5/1982 | European Pat. Off. . |
| 0050850A1 | 5/1982 | European Pat. Off. . |
| 0079022 | 5/1983 | European Pat. Off. . |
| 0090362 | 10/1983 | European Pat. Off. . |
| 180785 | 5/1986 | European Pat. Off. . |
| 812859 | 3/1982 | Finland . |
| 813283 | 4/1982 | Finland . |
| 813034 | 4/1982 | Finland . |
| 813422 | 5/1982 | Finland . |
| 2491469 | 5/1983 | France . |
| 3143946 | 1/1983 | Germany . |
| 3226768 | 5/1983 | Germany . |
| 3322530 | 1/1985 | Germany . |
| 64085 | 10/1982 | Israel . |
| 91974 | 5/1982 | Japan . |
| 77672 | 6/1982 | Japan . |
| 112359 | 7/1982 | Japan . |
| 198535 | 8/1985 | Netherlands . |
| 198702 | 9/1984 | New Zealand . |
| 81/5988 | 7/1982 | South Africa . |
| 82/8085 | 8/1982 | South Africa . |
| 832229 | 3/1983 | South Africa . |
| 2086390 | 5/1982 | United Kingdom . |
| 2095682 | 10/1982 | United Kingdom . |

OTHER PUBLICATIONS

Leonard et al., J. Am. Chem. Soc., 77, 439 (1955).
Leonard et al., J. Am. Chem. Soc., 78, 3457 (1956).
Leonard et al., J. Am. Chem. Soc., 78, 3463 (1956).
Leonard et al., J. Am. Chem. Soc., 81, 5627 (1959).
Koelsch et al., J. Org. Chem., 26, 1104 (1961).
Griot et al., Helv. Chim. Acta, 42, 121 (1959).
Bonnett et al., J. Chem. Soc., 2087 (1959).
Battersby et al., J. Chem. Soc., 4333 (1958).
Rosenblatt et al., The Chemistry Of Functional Groups. Supplement F: The Chemistry of Amino, Nitroso and Nitro Compounds And Their Derivatives. Part II, S. Patai, ed., Wiley & Sons: New York 1982, pp. 1100–1104.
L. W. Haynes, Enamines, A. G. Cook, ed., Marcel Decker, Inc.: 1969, pp. 68–79, 261–269, 413.
Fieser & Fieser, Reagents For Organic Synthesis, vol. 1, pp. 644–651 (1967).
Boehme et al., Iminium Salts in Organic Chemistry, Part I (E.C. Taylor, ed.), Wiley & Sons: New York, 1976, p. 143.
S. Dayagi et al., The Chemistry Of Functional Groups. The Chemistry Of The Carbon–Nitrogen Double Bond, S. Patai, ed., Wiley & Sons: New York, 1970, p. 119.

(List continued on next page.)

Primary Examiner—Kimberly Jordan
Attorney, Agent, or Firm—Finnegan, Henderson, Farabow, Garrett & Dunner

[57] ABSTRACT

The invention relates to combinations of angiotensin-converting enzyme inhibitors with calcium antagonists, processes for their preparation and their use as medicaments.

5 Claims, No Drawings

OTHER PUBLICATIONS

W. Greenlee et al., J. Med. Chem., 28, 434–442 (1985).
K. Ogawa et al., J. Chem. Soc., Perkin Trans. I, 3031–3035 (1982).
R. Bacon and D. Stewart, J. Chem. Soc. (C), 1384–1387 (1966).
R. Bacon et al., J. Chem. Soc. (C), 1388–1389 (1966).
Patchett et al., Nature, 288, 280–283 (1980).
Booth et al., Chemistry and Industry, 466–467 (1956).
Booth et al., J. Chem. Soc., Part I, 1050–1054 (1959).
Murakoshi et al., Chemical Abstracts, 61, 9465(e) (1964).
Cushman et al., Fed. Proc., 38 (13), 2778–2782 (1979).
Houben–Weytl, Methoden der Organischen Chemie, 7(2b), 1403–1404 (1976).
Katritskaya, Dzh. Lagorskaya Khimia Geterosikl. Soedin., Moskow 1963, pp. 155–158.
Anderson, Jr. et al., J. Org. Chem., 43(1), 54–57 (1978).
Bertho et al., "Synthesen In Der 2–Azabicyclo[0.3.3]–octan–Reihe", Chemische Berichte, 92(7), 2218–2235 (1959).
Farkas et al., J. Org. Chem., 22, 1261–1263 (1957).
Taylor et al., J. Org. Chem., 38(16), 2817–2821 (1973).
Taylor et al., Heterocycles, 25, 343–345 (1987).
English language translation of Mitzlaff et al., Liebig's Ann. Chem., 1713–1733 (1978).
Chem. Berichte 86: 1524–1528 (1953).
Quarterly Reviews 25: 323–341 (1971).
Chem. Abst. 49/1955/3009c.
Merke Index, 11th Ed. (1989), #8123.
Merke Index, 11th Ed. (1989), #3895.
Middeke et al., Nieren–und Hochdruckkrankbeiten, vol. 21(10):524–527 (1992).

COMBINATION OF ANGIOTENSIN-CONVERTING ENZYME INHIBITORS WITH CALCIUM ANTAGONISTS AS WELL AS THEIR USE IN DRUGS

This is a continuation of application Ser. No. 07/811,149, filed Dec. 20, 1991, now abandoned, which is a divisional application of Ser. No. 07/358,427, filed May 30, 1989, now U.S. Pat. No. 5,098,910, which is a continuation of application Ser. No. 07/102,660, filed Sep. 30, 1987, now abandoned.

The present invention relates to a combination of angiotensin-converting enzyme inhibitors (ACE inhibitors) with calcium antagonists as well as their use in drugs, especially in hypotensive drugs. ACE inhibitors are compounds which prevent the conversion of angiotensin I into the pressor-active angiotensin II. Such compounds are, for example, described in the following patent applications or patents:

U.S. Pat. Nos. 4,350,633, 4,344,949, 4,294,832, 4,350,704, EP-A 50,800, EP-A 31,741, EP-A 51,020, EP-A 49,658, EP-A 49,605, EP-A 29,488, EP-A 46,953 and EP-A 65,870.

They are also the subject of German Patent Applications P 3,226,768.1, P 3,151,690.4, P 3,210,496.0, p 3,211,397.8, P 3,211,676.4, P 3,227,055.0, P 3,242,151.6, P 3,246,503.3, P 3,246,757.5.

Their hyptotensive action is well documented. Calcium antagonists are compounds which influence the influx of calcium ions into cells, especially smooth muscle cells. Such compounds as well as their hypotensive activity are recorded in a large number of publications and patent applications.

Since the two groups of substances act on different blood pressure-regulation systems, in combined use the effect of one combination partner is raised by the other partner. In combined use this leads to a reduction in the dose of the combination partners, compared with single use. Thus the appearance of side effects known for the two classes of substance can be reduced or avoided.

Combinations of enalapril with calcium antagonists from the dihydropryridine class of structures are described in EP-A-1,807,85.

The following compounds of the formula I or their physiologically acceptable salts can be considered as ACE inhibitors:

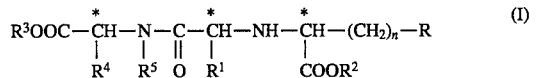

in which n=1 or 2,

R=hydrogen, an optionally substituted aliphatic radical with 1–8 carbon atoms, an optionally substituted alicyclic radical with 3–9 carbon atoms, an optionally substituted aromatic radical with 6–12 carbon atoms, an optionally substituted araliphatic radical with 7–14 carbon atoms, an optionally substituted alicyclic-aliphatic radical with 7–14 carbon atoms, a radical $OR^a$ or $SR^a$, wherein $R^a$ represents an optionally substituted aliphatic radical with 1–4 carbon atoms, an optionally substituted aromatic radical with 6–12 carbon atoms or an optionally substituted heteroaromatic radical with 5–12 ring atoms, $R^1$ is hydrogen, an optionally substituted aliphatic radical with 1–6 carbon atoms, an optionally substituted alicyclic radical with 3–9 carbon atoms, an optionally substituted alicyclic-aliphatic radical with 4–13 carbon atoms, an optionally substituted aromatic radical with 6–12 carbon atoms, an optionally substituted araliphatic radical with 7–16 carbon atoms, an optionally substituted heteroaromatic radical with 5–12 ring atoms or the side chain, protected if necessary, of a naturally occurring α-amino acid, $R^2$ and $R^3$ are the same or different and are hydrogen, an optionally substituted aliphatic radical with 1–6 carbon atoms, an optionally substituted alicyclic radical with 3–9 carbon atoms, an optionally substituted aromatic radical with 6–12 carbon atoms, an optionally substituted araliphatic radical with 7–16 carbon atoms and $R^4$ and $R^5$ together with the atoms carrying them form a heterocyclic bicyclic or tricyclic ring system with 5 to 15 carbon atoms.

The following groups can be especially considered as such ring systems:

Tetrahydroisoquinoline (A); decanhydroisoquinoline (B); octahydroindole (C); octahydrocyclopenta[b]pyrrole (D); 2-azaspiro [4,5]decane (E); 2-azaspiro[4,4]nonane (F); spiro [(bicyclo[2,2,1]heptane)-2,3'-pyrrolidine] (G); spiro[(bicyclo[2,2,2]octane)-2,3'-pyrrolidine] (H); 2-azatricyclo[4,3,0,1$^{6,9}$]decane (I); decanydrocyclohepta[b]-pyrrole (J); octahydroisoindole (K); octahydrocyclocopenta[c]pyrrole (L); 2,3,3a,4,5,7a-hexahydroindole (M); 2-azabicyclo[3,1,0]-hexane (N); hexahydrocyclopenta[b]pyrrole (O); which can all be optionally substituted. However, the unsubstituted systems are preferred.

In the compounds which possess several chiral atoms all possible diastereomers as racemates or as enantiomers, or mixtures of various diastereoisomers can be considered.

Esters of cyclic amino acids which can be considered exhibit the following structural formulae.

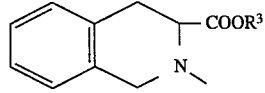

A

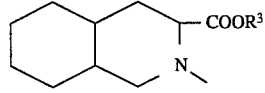

B

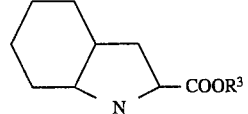

C

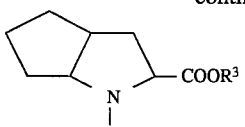
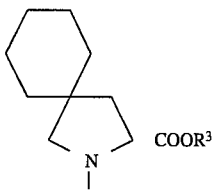
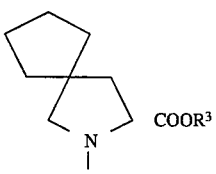
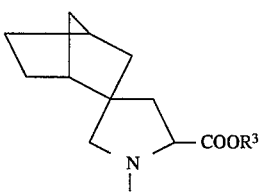
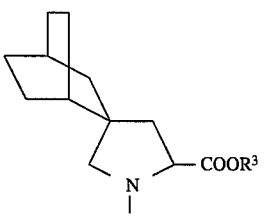
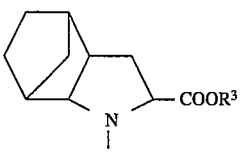
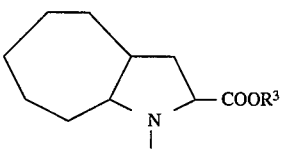
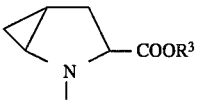
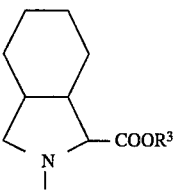

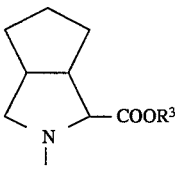
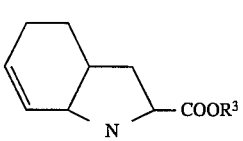
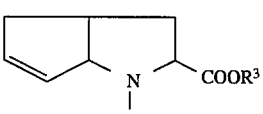

Particularly preferred are ACE inhibitors of the formula I, in which n=1 or 2

R is hydrogen,
alkyl with 1–8 carbon atoms,
alkenyl with 2–6 carbon atoms,
cycloalkyl with 3–9 carbon atoms,
aryl with 6–12 carbon atoms,
  which can be mono-, di- or tri-substituted by $(C_1-C_4)$-alkyl, $(C_1-C_4)$-alkoxy, hydroxy, halogen, nitro, amino, aminomethyl, $(C_1-C_4)$-alkylamino, di-$(C_1-C_4)$-alkylamino, $(C_1-C_4)$-alkanoylamino, methylenedioxy, cyano and/or sulfamoyl,
alkoxy with 1–4 carbon atoms,
aryloxy with 6–12 carbon atoms,
  which can be substituted as described above for aryl,
mono- or bi-cyclic heteroaryloxy with 5–7 or 8–10 ring atoms respectively, of which 1 to 2 ring atoms represent sulfur or oxygen atoms and/or 1 to 4 ring atoms represent nitrogen,
  which can be substituted as described above for aryl,
amino-$(C_1-C_4)$-alkyl,
$(C_1-C_4)$-alkanoylamino-$(C_1-C_4)$-alkyl,
$(C_7-C_{13})$-aroylamino-$(C_1-C_4)$-alkyl,
$(C_1-C_4)$-alkoxy-carbonylamino-$(C_1-C_4)$-alkyl,
$(C_6-C_{12})$-aryl-$(C_1-C_4)$-alkoxycarbonylamino-$(C_1-C_4)$-alkyl,
$(C_6-C_{12})$-aryl-$(C_1-C_4)$-alkylamino-$(C_1-C_4)$-alkyl,
$(C_1-C_4)$-alkylamino-$(C_1-C_4)$-alkyl,
di-$(C_1-C_4)$-alkylamino-$(C_1-C_4)$-alkyl,
guanidino-$(C_1-C_4)$-alkyl,
imidazolyl, indolyl,
$(C_1-C_4)$-alkylthio,
$(C_1-C_4)$-alkylthio-$(C_1-C_4)$-alkyl,
$(C_6-C_{12})$-arylthio-$(C_1-C_4)$-alkyl,
  which can be substituted in the aryl part as described above for aryl,
$(C_6-C_{12})$-aryl-$(C_1-C_4)$-alkylthio,
  which can be substituted in the aryl part as described above for ayl,
carboxy-$(C_1-C_4)$-alkyl,
carboxy, carbamoyl, carbamoyl-($C_1$–$C_4$)-alkyl,
($C_1$–$C_4$)-alkoxy-carbonyl-($C_1$–$C_4$)-alkyl,
($C_6$–$C_{12}$)-aryloxy-($C_1$–$C_4$)-alkyl,
  which can be substituted in the aryl part as described above for aryl, or
($C_6$–$C_{12}$)-aryl-($C_1$–$C_4$)-alkoxy,
  which can be substituted in the aryl part as described above for aryl,
$R^1$ is hydrogen,
alkyl with 1–6 carbon atoms,
alkenyl with 2–6 carbon atoms,
alkynyl with 2–6 carbon atoms,
cycloalkyl with 3–9 carbon atoms,
cycloalkenyl with 5–9 carbon atoms,
($C_3$–$C_9$)-cycloalkyl-($C_1$–$C_4$)-alkyl,
($C_5$–$C_9$)-cyclalkenyl-($C_1$–$C_4$)-alkyl,
optionally partially hydrogenated aryl with 6–12 carbon atoms, which can be substituted as described above for R,
($C_6$–$C_{12}$)-aryl-($C_1$–$C_4$)-alkyl or ($C_7$–$C_{13}$)-aroyl-($C_1$ or $C_2$)-alkyl
  both of which can be substituted as the previous aryl,
mono- or bi-cyclic, optionally partially hydrogenated heteraryl with 5–7 or 8–10 ring atoms respectively, of which 1 to 2 ring atoms represent sulfur or oxygen atoms and/or 1 to 4 ring atoms represent nitrogen atoms,
  which can be substituted as the previous aryl, or
the optionally protected side chain of a naturally occurring α-amino acid $R^1$—CH($NH_2$)-COOH,
$R^2$ and $R^3$ are the same or different and are hydrogen,
alkyl with 1–6 carbon atoms,
alkenyl with 2–6 carbon atoms,
di-($C_1$–$C_4$)-alkylamino-($C_1$–$C_4$)-alkyl,
($C_1$–$C_5$)-alkanoyloxy-($C_1$–$C_4$)-alkyl,
($C_1$–$C_6$)-alkoxy-carbonyloxy-($C_1$–$C_4$)-alkyl,
($C_7$–$C_{13}$)-aroyloxy-($C_1$–$C_4$)-alkyl,
($C_6$–$C_{12}$)-aryloxycarbonyloxy-($C_1$–$C_4$)-alkyl,
aryl with 6–12 carbon atoms,
($C_6$–$C_{12}$)-aryl-($C_1$–$C_4$)-alkyl,
($C_3$–$C_9$)-cycloalkyl or
($C_3$–$C_9$)-cycloalkyl-($C_1$–$C_4$)-alkyl, and
$R^4$ and $R^5$ have the meaning given above.

Particularly preferred are compounds of the formula I, in which
n=1 or 2,
R is ($C_1$–$C_6$)-alkyl, ($C_2$–$C_6$)-alkenyl, ($C_3$–$C_9$)-cycloalkyl, amino-($C_1$–$C_4$)-alkyl, ($C_2$–$C_5$)-acylamino-($C_1$–$C_4$)-alkyl, ($C_7$–$C_{13}$)-aroylamino-($C_1$–$C_4$)-alkyl, ($C_1$–$C_4$)-alkoxy-carbonylamino-($C_1$–$C_4$)-alkyl, ($C_6$–$C_{12}$)-aryl-($C_1$–$C_4$)-alkoxycarbonylamino-($C_1$–$C_4$)-alkyl, ($C_6$–$C_{12}$)-aryl, which can be ono-, di- or trisubstituted by ($C_1$–$C_4$)-alkyl,($C_1$–$C_4$)-alkoxy, hydroxy, halogen, nitro, amino ($C_1$–$C_4$)-alkylamino, di-($C_1$–$C_4$)-alkylamino and/or methylenedioxy, or 3-indolyl, especially methyl, ethyl, cyclohexyl, tert.-butoxycarbonylamino-($C_1$–$C_4$)-alkyl, benzoyloxycarbonylamino-($C_1$–$C_4$)-alkyl, or phenyl, which can be mono- or di-substituted or, in the case of methoxy, trisubstituted by phenyl, ($C_1$–$C_2$)-alkyl, ($C_1$ or $C_2$)-alkoxy, hydroxy, fluoro, chloro, bromo, amino, ($C_1$–$C_4$)-alkylamino, di-($C_1$–$C_4$)-alkylamino, nitro and/or methylenedioxy, $R^1$ is hydrogen or ($C_1$–$C_6$)-alkyl, which can be optionally substituted by amino, ($C_1$–$C_6$)-acylamino or benzoylamino, ($C_2$–$C_6$)-alkenyl, ($C_3$–$C_9$)-cycloalkyl, ($C_5$–$C_9$)-cycloalkenyl, ($C_3$–$C_7$)-cycloalkyl-($C_1$–$C_4$)-alkyl, ($C_6$–$C_{12}$)-aryl or partially hydrogenated aryl, which can each be substituted by ($C_1$–$C_4$)-alkyl, ($C_1$ or $C_2$)-alkoxy or halogen, ($C_6$–$C_{12}$)-aryl-($C_1$ to $C_4$)-alkyl or ($C_7$–$C_{13}$)-aroyl-($C_1$–$C_2$)-alkyl, which can be both be substituted as defined previously in the aryl radical, a mono- or bi-cyclic heterocyclic radical with 5 to 7 or 8 to 10 ring atoms respectively, or which 1 to 2 ring atoms represent sulfur or oxygen atoms and/or 1 to 4 ring atoms represent nitrogen atoms, or a side chain of a naturally occurring, optionally protected α-amino acid, but especially hydrogen, ($C_1$–$C_3$)-alkyl, ($C_2$ or $C_3$)-alkenyl, the optionally protected side chain of lysine, benzyl, 4-methoxybenzyl, 4-ethoxybenzyl, phenethyl, 4-aminobutyl or benzoylmethyl, $R^2$ and $R^3$ are the same or different and are hydrogen, ($C_1$–$C_6$)-alkyl, ($C_2$–$C_6$)-alkenyl or ($C_6$–$C_{12}$)-aryl-($C_1$–$C_4$)-alkyl, but especially hydrogen, ($C_1$–$C_4$)-alkyl or benzyl, and $R^4$ and $R^5$ have the meanings given above.

Under aryl is to be understood here and also in the following as preferably optionally substitute diphenyl, biphenylyl or naphthyl. The same applies to aryl-derived radicals such as aryloxy, arylthio. Aroyl is understood as especially benzoyl. Aliphatic radicals can be straight-chain or branched.

Under a mono- or bi-cyclic heterocyclic radical with 5 to 7 or 8 to 10 ring atoms respectively, or which 1 to 2 ring atoms represent sulfur or oxygen atoms and/or of which 1 to 4 ring atoms represent nitrogen atoms, is understood for example thienyl, benzo[b]thienyl, furyl, pyranyl, benzofuryl, pyrrolyl, imidazolyl, pyrazolyl, pyridyl, pyrimidinyl, pyridazinyl, indazolyl, isoindolyl, indolyl, purinyl, quinolizinyl, isoquinolinyl, phthalazinyl, naphthyridinyl, quinoxalinyl, quinazolyl, cinnolinyl, pteridinyl, oxazolyl, isoxazolyl, thiazolyl or isothiazolyl. These radicals can also be partially or completely hydrogenated.

Naturally occurring -amino acids are described e.g. in Houben-Weyl, Methoden der Organischen Chime [methods of Organic Chemistry], volume XV/1 and XV/2.

If $R^1$ represents a side chain of a protected naturally occurring α-amino acid, as e.g. protected Ser, Thr, Asp, Asn, Glu, Gln, Arg, Lys, Hyl, Cys, Orn, Cit, Hyr, Trp, His or Hyp, the groups usual as protective groups in peptide chemistry are preferred (see Houben-Weyl, volume SV/1 and XV/2). In the case where $R^1$ is the protected lysine side chain, the known amino-protecting groups and especially Z, Boc or ($C_1$–$C_6$)-alkanoyl are preferred. As O-protective groups for tyrosine ($C_1$–$C_6$)-alkyl is preferred, particularly methyl or ethyl.

Particularly preferred compounds 2-[N-(1-S-ethoxycarbonyl-3-phenylpropyl)-S-alanyl]-(1S,3S,5S)-2-azbicyclo-[3,3,0]octane-3-carboxylic acid (ramipril), 1-[N-(1-S-ethoxycarbonyl-3-phenylpropyl)-S-alanyl]-( 2S,3aR,7aS)-octahydro[1H]indole-2-carboxylic acid (trandolapril) as well as 2-[N-(1-S-ethoxycarbonyl-3-phenylpropyl)-S-alanyl]-1,2,3,4-tetrahydroisoquinoline-3-S-carboxylic acid (quinapril).

The ACE inhibitors of the formula I can be prepared by reacting their fragments with one another in a suitable solvent optionally in the presence of a base and/or a coupling agent, optionally reducing resulting intermediate unsaturated compounds, such as Schiff bases, removing protective groups temporarily introduced for the protection of reactive groups, optionally esterifying compounds of the formula I with (a) free carboxyl group(s) and optionally converting the obtained compounds into their physiologically acceptable salts.

In the above manner, for example, compounds of the formula V can be reacted with compounds of the formula VI.

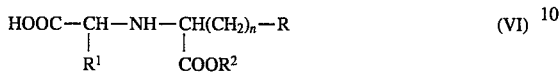

The reaction of these compounds can be carried out, for example, in analogy to known peptide coupling methods in an organic solvent such DMF, CH$_2$Cl$_2$, DMA in the presence of coupling agents, such as carbodiimides (e.g. dicyclohexylcarbodi-imide), diphenylphosphoaryl azide, alkane-phosphoric acid anhydrides, dialkylphosphinic acid anhydrides or N,N-succinimidyl carbonates in a solvent such as CH$_3$CN. Amino groups in compounds of the formula V can be activated with tetraethyl diphosphite. The compounds of the formula VI can be converted into active esters (e.g. with 1-hydroxybenzotriazole), mixed anhydrides (e.g. with chloroformates), azides or carbodiimide derivatives and thus activated (see Schroder, Lübke. The Peptides, volume 1, New York 1965, pages 76–136). The reaction is preferably performed between –20° C. and the boiling point of the reaction mixture.

Likewise compounds of the formula VII can be reacted with compounds of the formula VIII with the formation of compounds of the formula I,

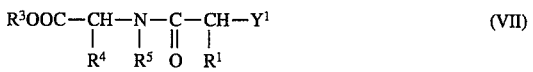

wherein either Y$^1$ represents amino and Y$^2$ a leaving group or Y$^1$ represents a leaving group and Y$^2$ amino. Suitable leaving groups are e.g. Cl, Br, I, alkylsulfonyloxy or arylsulfonyloxy.

Alkylations of this type are suitable performed in water or an organic solvent such as a lower aliphatic alcohol (such as ethanol), benzyl alcohol, acetonitrile, nitromethane or a glycol ether at a temperature between –20° C. and the boiling point of the reaction mixture in the presence of a base such as an alkali metal hydroxide or an organic amine.

In addition, compounds of the formula IX can be condensed with compounds of the formula X,

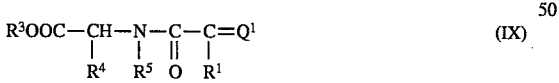

wherein either Q$^1$ represents amino+hydrogen and Q$^2$ oxo or Q$^1$ represents oxo and Q$^2$ amino+hydrogen.

The condensation is suitably performed in water or an organic solvent, such as a lower aliphatic alcohol, at a temperature between –20° C. and the boiling point of the reaction mixture in the presence of a reducing agent, such as NaBH$_3$CN, compounds of the formula I being directly obtained. The Schiff bases or enamines resulting as by-products can, however, also be reduced, after previous isolation, with formation of compounds of the formula II, for example by hydrogenation in the presence of a transition metal catalyst.

Finally, the reaction of compounds of the formula IX (Q$^1$=H+NH$_2$) with compounds of the formula XI or their reaction with compounds of the formulae XII and XIII suitably in the presence of a base, such as a sodium alkoxide, in an organic solvent, such as a lower alcohol, at a temperature between –10° C. and the boiling point of the reaction mixture also leads to compounds of the formula II (n=2),

the resulting intermediate Schiff bases being reduced as described above and a carbonyl group being converted by reduction to methylene (for example with a complex hydride).

In the abovementioned formulae V–XIII, R–R$^5$ and n are as defined in formula I. Temporarily introduced protective groups for the protection of reactive groups not participating in the reaction are removed after the end of the reaction by a method know per se (see Schröder, Lübke, Loc cit., pages 1–75 and 246–270; Greene, "Protective Groups in Organic Synthesis", New York 1981).

As calcium antagonists the compounds of the formula II can be considered

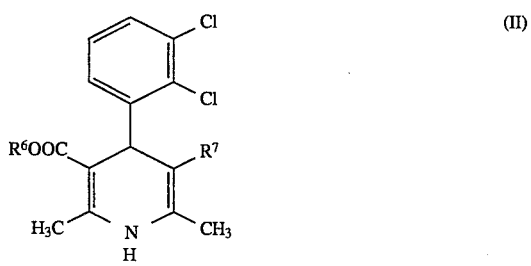

in which R$^6$ is methyl, ethyl or isopropyl and R$^7$ is methoxycarbonyl, ethoxycarbonyl or 1,2,4-oxadiazol-3-yl, as well as their physiologically acceptable salts, or compounds of the formula III

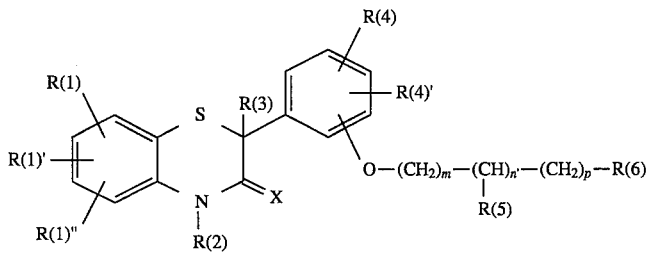

(III)

in which
- R(1), R(1)' and R(1)" are the same or different and independently are hydrogen, $(C_1-C_4)$-alkyl, $(C_1-C_3)$-alkoxy, halogen, nitro, hydroxy, acetamido or amino,
- R(2) is hydrogen, $(C_1-C_{10})$-alkyl, straight-chain or branched, $(C_3-C_{10})$-alkenyl, straight-chain or branched, phenyl which can be optionally substituted by one, two or three substituents from the group $(C_1-C_4)$-alkyl, $(C_1-C_3)$-alkoxy, halogen, $(C_1-C_2)$-alkylenedioxy or nitro, phenyl-$(C_1-C_4)$-alkyl, in which the phenyl ring can be substituted by one, two or three substitutents from the groups $(C_1-C_4)$-alkyl, $(C_1-C_3)$-alkoxy, halogen, $(C_1-C_2)$-alkylenedioxy or nitro, or is $(C_4-C_8)$-cycloalkyl-$(C_1-C_4)$-alkyl, or $(C_4-C_8)$-cycloalkyl,
- R(3) is hydrogen, $(C_1-C_{10})$-alkyl, straight-chain or branched, $(C_3-C_{10})$-alkenyl, straight-chain or branched, phenyl-$(C_1-C_4)$-alkyl, in which the phenyl radical can be substituted by one, two or three substituents from the group $(C_1-C_4)$-alkyl, $(C_1-C_3)$-alkoxy, halogen, $(C_1-C_2)$-alkylenedioxy or nitro, or is $(C_4-C_8)$-cycloalkyl or $(C_4-C_8)$-cyclaokyl-$(C_1-C_4)$-alkyl,
- R(4) and R(4)' are the same or different and independently are hydrogen, $(C_1-C_4)$-alkyl, $(C_1-C_3)$-alkoxy, halogen, nitro, hydroxy, acetamido or amino,
- R(5) is hydrogen or $(C_1-C_3)$-alkyl,
- R(6) is a part structure from the following group,

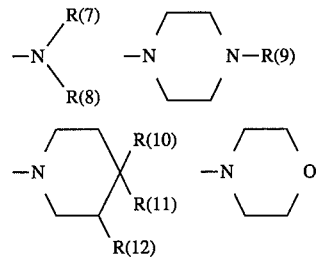

wherein
- R(7) and R(8) are the same or different and independently are hydrogen, $(C_1-C_{10})$-alkyl, $(C_4-C_8)$-cyclaokyl, $(C_4-C_8)$-cyclalkyl-$(C_1-C_4)$-alkyl, phenyl-$(C_1-C_6)$-alkyl, in which the phenyl radical can be substituted by one, two or three radicals from the group $(C_1-C_4)$-alkyl, $(C_1-C_4)$-alkoxy, $(C_1-C_2)$-alkylenedioxy, halogen or hydroxy, or pyridyl-$(C_1-C_4)$-alkyl,
- R(9) is hydrogen, $(C_1-C_{10})$-alkyl, straight-chain or branched, phenyl in which the phenyl radical can be substituted by one, two or three radicals from the group $(C_1-C_4)$-alkyl, $(C_1-C_4)$-alkoxy, $(C_1-C_2)$-alkylenedioxy, halogen or hydroxy, phenyl-$(C_1-C_4)$-alkyl in which the phenyl radical can be substituted by one, two or three radicals from the group $(C_1-C_4)$-alkyl, $(C_1-C_4)$-alkoxy, $(C_1-C_2)$-alkylenedioxy, halogen or hydroxy, or is pyridyl, pyrimidinyl, $(C_1-C_5)$-alkanoyl, phenyl-$(C_1-C_4)$-alkanoyl, benzoyl, in which each phenyl radical can be substituted by one, two or three radicals from the group $(C_1-C_4)$-alkyl, $(C_1-C_4)$-alkoxy, $(C_1-C_2)$-alkylenedioxy, halogen or hydroxy,
- R(10) is hydrogen, $(C_1-C_{10})$-alkyl, phenyl which can be substituted by one, two or three radicals from the group $(C_1-C_4)$-alkyl, $(C_1-C_4)$-alkoxy, $(C_1-C_2)$-alkylenedioxy, halogen or hydroxy, or phenyl-$(C_1-C_4)$-alkyl, in which the phenyl radical can be substituted by one, two or three radicals from the group $(C_1-C_4)$-alkyl, $(C_1-C_4)$-alkoxy, $(C_1-C_2)$-alkylenedioxy, halogen or hydroxy,
- R(11) is hydrogen, hydroxy, $(C_1-C_4)$-alkoxy, or together with R(12) is a bond, and
- R(12) is hydrogen or together with R(11) is a bond; and in which formula I furthermore
- m is 1, 2, 3, or 4,
- n' is 0 or 1,
- p is 0, 1, 2, 3, or 4 and
- X is oxygen or two hydrogen atoms, or their physiologically acceptable salts, or compounds of the formula IV

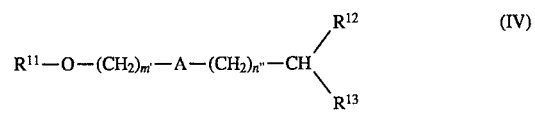

in which:
- $R^{11}$ is $(C_3-C_8)$-cycloalkyl, $(C_2-C_6)$-alkenyl, straight-chain or branched $(C_5-C_8)$-cycloalkenyl,

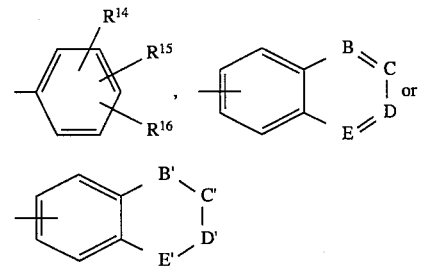

wherein
- $R^{14}$, $R^{15}$ and $R^{16}$ are the same or different and independently are hydrogen, $(C_1-C_6$-alkyl, $(C_3-C_8)$-cycloalkyl, hydroxy, $(C_1-C_4)$-alkoxy, $(C_1-C_4)$-alkylthio, F, Cl, Br, I, nitro, cyano, trifluormethyl, formyl, carboxy, $(C_1-C_6)$-alkoxycarbonyl, $(C_1-C_6)$-acyl, carbamoyl, N,N-mono- or di-$(C_1-C_6)$-alkyl-carbamoyl, sulfo, $(C_1-C_6)$-alkoxysulfonyl, sulfamoyl, N-mono- or N,N-di-$(C_1-C_6)$-alkysulfamoyl, $(C_1-C_6)$-alkylsulfinyl, $(C_1-C_6)$-alkylsulfonyl, amino, unsubstituted or substituted with one or two identical or different $(C_1-C_6)$-alkyl, $(C_1-C_6)$-acyl or aryl, preferably phenyl, groups, B, C, D and E are the same or different and independently are methine or nitrogen, B', C', D' and E' are the same or different and independently are methylene, carbonyl, imino, unsubstituted or substituted on the nitrogen by $(C_1-C_6)$-alkyl, $(C_1-C_6)$-acyl or aryl, preferably phenyl, $R^{12}$ and $R^{13}$ are the same or different and independently are phenyl, phenyl-$(C_1-C_4)$-alkyl, in which each phenyl ring is unsubstituted or substituted by one, two or three substituents from the group $(C_1-C_4)$-alkyl, $(C_1-C_4)$-alkoxy, F, Cl, Br, I, cyano, nitro or trifluoromethyl, A is an amine

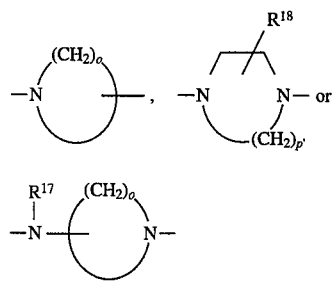

wherein $R^{17}$ is hydrogen, $(C_1-C_6)$-alkyl, aryl, preferably phenyl, $R^{18}$ is hydrogen, $(C_1-C_6)$-alkyl, formyl, $(C_1-C_6)$-acyl, carboxyl, $(C_1-C_6)$-alkoxycarbonyl, carbamoyl, N-mono- or N,N-di-$(C_1-C_6)$-alkylcarbamoyl, o is 3, 4, 5, 6, or 7, p' is 2 or 3, m' is 2, 3, or 4, n" is 1, 2, 3, or 4 and as well as their physiologically acceptable salts.

Preferred are compounds of the formula III, as defined previously, in which

R(2) is hydrogen, methyl, ethyl, propyl, isopropyl or phenyl,

R(3) is methyl, ethyl, propyl, isopropyl, butyl, sec.butyl, isobutyl, cyclopentyl or cyclohexyl, R(4) is hydrogen, methoxy, methyl or chloro, R(6) is a part structure from the following group

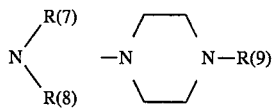

R(7) is methyl,

R(8) is as defined above,

R(9) is phenyl-$(C_1-C_4)$-alkyl, in which the phenyl radical can be substituted by one, two or three radicals from the group $(C_1-C_2)$-alkoxy, $(C_1-C_2)$-alkylenedioxy or hydroxy, m is 3, p is 0 or 1 and their physiologically acceptable salts, as well as compounds of the formula IV, in which $R^{11}$ is cyclohexyl, phenyl, which is unsubstituted or substituted by methyl, tert-butyl, methoxy, fluoro, nitro, cyano or trifluoromethyl, or is naphthyl, quinolinyl or isoquinolinyl, $R^{12}$ and $R^{13}$ are the same or different and independently are phenyl which is unsubstituted or substituted by fluoro or trifluoromethyl, and A is an amine

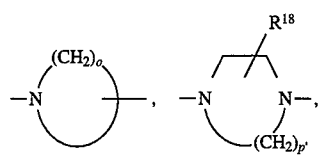

wherein $R^8$ is hydrogen, o is 5, p' is 2, m' is 2 and n" is 3, as well as their physiologically acceptable salts.

Particularly preferred are 4-(2,3-dichlorophenyl)-2,6-dimethyl-3-methoxycarbonyl-5-ethoxycarbonyl- 1,4-dihydropyridine (felodinpine, formula II); 4-(2,4-dichlorophenyl)-2,6-dimethyl-3-(1,2,4-oxadiazol-3-yl)-5-isopropoxycarbonyl-1,4-dihydropyridine (formula II); R(+)-3,4-dihydro-2-isopropyl-4-methyl-2-[2-[4-[4-[2-(3,4,5-trimethoxyphenyl)-ethyl]-piperazinyl]-butoxy]-phenyl]-2H-1,4-benzothiazin-3-one (formula III); 1-[2-(4-trifluoromethyl)-phenoxy]-ethyl-4-[4-bis-(4-fluorophenyl)-butyl]-piperazine (formula IV), as well as their physiologically acceptable salts with acids.

Of very particular interest are the following combinations:

Ramipril+felodipine or ramipril+4-(2,3-dichlorophenyl)-2,6-dimethyl-3-(1,2,4-oxodiazol-5-yl)-5-isopropoxycarbonyl-1,4-dihydropyridine or ramipril+R-(+)-3,4-dihydro-2-isopropyl-4-methyl-2-[2-[4-[2-(3,4,5-trimethoxyphenyl)-ethyl]-piperazineyl]-butoxy]-phenyl]-2H-1,4-benzothiazine-3-one or ramipril+1-[2-(4-trifluoromethyl)-phenoxy]-ethyl-4-[4-bis-(4-fluorophenyl)-butyl]-piperazine or trandolapril+felodipine or trandolapril+4-(2,3-dichlorophenyl)-2,6-dimethyl-3-(1,2,4-oxadiazol-3-yl)-5-isopropoxycarbonyl-1,4-dihydropyridine or trandolapril+R-(+)-3,4-dihydro-2-isopropyl-4-methyl-2-[2-[4-[4-[2-(3,4,5-trimethoxyphenyl)-ethyl]-piperzinyl]-butoxy]-phenyl]-2H-1,4-benzothiazine-3-one or trandolapril+1-[2-(4-trifluoromethyl)-phenoxy]-ethyl-4-[4-bis-(4-fluorophenyl)-butyl]-piperazine or quinapril+felodipine or quinapril+4-(2,3-dichlorophenyl)-2,6-dimethyl-3-(1,2,4-oxodiazol-5-yl)-5-isopropoxycarbonyl-1,4-dihydropyridine or quinapril+R-(+)-3,4-dihydro-2-isopropyl-4-methyl-2-[2-[4-[2-(3,4,5-trimethoxyphenyl)-ethyl]-piperazinyl]-butoxy]-phenyl]-2H-1,4-benzothiazine-3-one or quinapril+1-[2-(4-trifluoromethyl)-phenoxy]-ethyl-4-[4-bis-(4-fluorophenyl)-butyl]-piperazine as well as the physiologically acceptable salts of each of the above single components, in as far as these form salts.

The invention also relates quite generally to products, which contain:

a) an ACE inhibitor of the formula I or its physiologically acceptable salts and b) a calcium antagonist or its physiologically acceptable salts as a combination preparation for simultaneous, separate or periodic regulated use in the treatment of high blood pressure.

The pharmaceutical compositions can be prepared, for example, by intimately mixing the single components as powders, or by dissolving the single components in a suitable solvent such as, for example, a lower alcohol and then removing the solvent.

The ratio of the active agents in the combinations and compositions according to the invention is preferably 1–15 parts by weight of ACE inhibitor to 15 - 1 parts by weight of calcium antagonist. The combinations and compositions according to the invention contain altogether preferably 0.5–99.5% by weight, particularly 4–96% by weight, of these active agents.

As mentioned above, the compositions and combinations according to the invention can be used in drugs, particularly for the treatment of high blood pressure, coronary insufficiency and coronary heart disease.

The compositions and combinations according to the invention can be orally or parenterally administered in a corresponding pharamceutical composition. For oral use, the active compounds are mixed with the additives usual for this purpose, such as carriers, stabilizers or inert diluents, and converted by the usual methods into suitable forms for administration, such as tablets, dragees, cylindrical capsules, aqueous, alcoholic or oily suspensions or aqueous, alcoholic or oily solutions. As inert carrier e.g. gum arabic, magnesium carbonate, potassium phosphate, lactose, glucose or starch, particularly maize starch, can be used. In this case, the composition can be formed both as dry or moist granules. Vegetable and animal oils, such as sunflower oil or code liver oil for example, can be considered as oily carriers or solvents.

For subcutaneous or intravenous administration, the active substances or their physiologically acceptable salts are brought into solution, suspension or emulsion, optionally with the usually employed substances such as solubilizers, emulsifiers or other auxiliaries. As solvents for the active combinations and the corresponding physiologically acceptable salts can be considered e.g.: water, physiological salt solutions or alcohols, e.g. ethanol, propane-diol or glycerol, besides also sugar solutions such as glucose or mannitol solutions or also a mixture of the various solvents mentioned.

As salts of the compounds of the formulae I to IV can be considered, depending on the acid or basic nature of these compounds, alkali or alkaline earth metal salts or salts with physiologically acceptable amines or salts with inorganic or organic acids such as e.g. HCl, HBr, $H_2SO_4$, maleic acid, fumaric acid, tartaric acid and citric acid.

The following examples serve to illustrate the present invention, without restricting it thereto:

EXAMPLE 1

Preparation of an oral combination product from ramipril and felodipine 1,000 tablets, which contain 2 mg of ramipril and 6 mg of felodipine are prepared as follows:

| | |
|---|---|
| ramipril | 2 g |
| felodipine | 6 g |
| maize starch | 140 g |
| gelatine | 7.5 g |
| microcrystalline cellulose | 2.5 g |
| magnesium stearate | 2.5 g |

The two active agents are mixed with an aqueous gelatine solution. The mixture is dried and ground to granules. Microcrystalline cellulose and magnesium stearate are mixed with the granules. The granules so obtained are compressed into 1,000 tablets, each tablet containing 2 mg of ramipril and 6 mg of felodipine.

EXAMPLE 2

Preparation of an oral combination product from trandolapril and felodipine 1,000 tablets, which contain 3 mg of trandolapril and 5 mg of felodipine are prepared as follows:

| | |
|---|---|
| trandolapril | 3 g |
| felodipine | 5 g |
| maize starch | 130 g |
| gelatine | 8.0 g |
| microcrylstalline cellulose | 2.0 g |
| magnesium stearate | 2.0 g |

The two active agents are mixed with an aqueous gelatine solution. The mixture is dried and ground to granules. Mirocrystalline cellulose and magnesium stearate are mixed with the granules. The granules so obtained are compressed into 1,000 tablets, each tablet containing 3 mg of trandolapril and 5 mg of felodipine.

EXAMPLE 3

Preparation of an oral combination product from quinapril and felodinpine 1,000 tablets, which contain 2.5 mg of quinapril and 6 mg of felodipine are prepared as follows:

| | |
|---|---|
| quinapril | 2.5 g |
| felodipine | 5 g |
| maize starch | 150 g |
| gelatine | 7.5 g |
| microcrystalline cellulose | 2.5 g |
| magnesium stearate | 2.5 g |

The two active agents are mixed with an aqueous gelatine solution. The mixture is dried and ground to granules. Microcrystalline cellulose and magnesium stearate are mixed with the granules. The granules so obtained are compressed into 1,000 tablets, each tablet containing 2.5 mg of quinapril and 5 mg of felodipine.

We claim:

1. A pharmaceutical composition, comprising a) 1-[N-(1-S-1-[N-(1-S-ethoxycarbonyl-3-phenylpropyl)-S-alanyl]-(2S,3aR,7aS)-octahydro[1H]indole-2-S-carboxylic acid (trandolapril) or a physiologically acceptable salt thereof in combination with b) 4-( 2,3-dichlorophenyl)-2,6-dimethyl-3-methoxycarbonyl-5-ethoxycarbonyl- 1,4-dihydropyridine (felodine) or a physiologically acceptable salt thereof, wherein a) and b) are present in a combined amount more effective to lower blood pressure than the individual amounts of either a) or b) administered separately.

2. A method for the treatment of high blood pressure, which comprises administering to a host in recognized need thereof an effective amount of a pharmaceutical composition as claimed in claim 1.

3. A method for the treatment of cardiac insufficiency, which comprises administering to a host in recognized need thereof an effective amount of a pharmaceutical composition as claimed in claim 1.

4. A method for the treatment of coronary heart disease, which comprises administering to a host in recognized need thereof an effective amount of a pharmaceutical composition as claimed in claim 1.

5. A pharmaceutical composition as claimed in claim 1, wherein said composition comprises a physiologically acceptable carrier.

* * * * *

UNITED STATES PATENT AND TRADEMARK OFFICE
CERTIFICATE OF CORRECTION

PATENT NO. : 5,500,434
DATED : March 19, 1996
INVENTOR(S) : BECKER et al.

It is certified that error appears in the above-identified patent and that said Letters Patent is hereby corrected as shown below:

<u>In the Claims</u>, claim 1, column 14, lines 41-42, "1-[N-(1-S-1-[N-(1-S-ethoyxycarbonyl-3-phenylpropyl)-S-alanyl]-(2S,3aR,7aS)-octahydro[1H]indole-2-S-carboxylic" should be corrected to --"1-[N-(1-S-ethyxycarbonyl-3-phenylpropyl)-S-alanyl]-(2S,3aR,7aS)-octahydro[1H]indole-2- S-carboxylic--; and claim 1, column 14, line 47, "felodine" should be corrected to -- felodipine--.

Signed and Sealed this

Twenty-sixth Day of May, 1998

Attest:

BRUCE LEHMAN

*Attesting Officer*  *Commissioner of Patents and Trademarks*